United States Patent [19]

Nakagawa

[11] Patent Number: Plant 5,480

[45] Date of Patent: May 28, 1985

[54] NECTARINE TREE—N15500

[75] Inventor: Glenn T. Nakagawa, 15500 S. Chestnut Ave., Fresno, Calif. 93725

[73] Assignees: Glenn T. Nakagawa, Fresno; Allan T. Nakagawa, Selma, both of Calif.

[21] Appl. No.: 535,734

[22] Filed: Sep. 26, 1983

[51] Int. Cl.[3] ..... A01H 5/03

[52] U.S. Cl. ..... Plt./41

[58] Field of Search ..... Plt./41

*Primary Examiner*—Robert E. Bagwill

*Attorney, Agent, or Firm*—Roger B. Webster

[57] ABSTRACT

A nectarine tree which is large, vigorous, upright when young and spreading at maturity; foliated with medium size, lanceolate, dark green leaves having a broadly crenate margin and medium size, reniform, uniform, alternate stem glands; blooms from hardy, conic flower buds of medium size and length, the bloom time being medium compared with other varieties and very similar to Flamekist; the flowers being abundant, large, light pink, and showy; and is a regular and productive bearer of late-ripening, large, uniform, clingstone fruit nearly round to ovate in lateral aspect and globose in axial aspect; the fruit having red-blushed-over-yellow, glossy skin, yellow flesh, and a dark brown stone.

1 Drawing Figure

BACKGROUND OF THE VARIETY

1. Field of the Invention

In the operation and maintenance of a ranch—of which I am an owner—located near Fresno, Fresno County, Calif., I frequent such ranch for the purpose of inspection, soil cultivation, irrigation, and harvesting. Against the background of such activities, and during a harvest period, the present variety of nectarine tree was discovered by me.

2. Classification of the Variety

The present variety of nectarine tree is embraced by Class 41, Plants, of the U.S. Patent Office Manual of Classification.

3. Prior Varieties

Among existing varieties of nectarine trees which are known to me, and mentioned herein, is the Flamekist (unpatented).

ORIGIN OF THE VARIETY

The present variety of nectarine tree was discovered by me growing—as a mutation involving an entire tree—in an orchard of Flamekist nectarine trees on the aforesaid ranch. More particularly, I observed, during harvest, that a tree in such orchard (and which is the present variety) bore certain new and distinct characteristics, especially in relation to the appearance and ripening period of the fruit. Subsequently, under close and continuing observation of such singular tree, I confirmed such characteristics and determined to asexually reproduce the tree in anticipation of commercial growing thereof.

ASEXUAL REPRODUCTION OF THE VARIETY

The present variety of nectarine tree was asexually reproduced, on the aforesaid ranch and under my direction, by grafting onto peach rootstock, and, in maturity, trees so reproduced ran true to the original tree (mutation) in all respects.

SUMMARY OF THE VARIETY

The present variety of nectarine tree is, characteristically, large, vigorous, upright when young and spreading at maturity; foliated with medium size lanceolate, dark green leaves having a broadly crenate margin and medium size, reniform, uniform, alternate stem glands; blooms from hardy, conic flower buds of medium size and length, the bloom time being medium compared with other varieties and very similar to Flamekist; the flowers being abundant, large, light pink, and showy; and is a regular and productive bearer of late-ripening, large, uniform, clingstone fruit nearly round to ovate in lateral aspect and globose in axial aspect; the fruit having red-blushed-over-yellow, glossy skin, yellow flesh, and a dark brown stone.

The present variety of nectarine tree is further characterized by the later maturity of the fruit in comparison to the Flamekist. On the aforesaid ranch, and as exemplary, the first picking and last picking of the fruit of the Flamekist were, respectively, Aug. 12, 1982, and Aug. 26, 1982, whereas the first picking and the last picking of the fruit of the present variety were, respectively, Aug. 24, 1982, and Sept. 3, 1982. This is indicative that the present variety of nectarine tree is about twelve days later, in fruit maturity, than the Flamekist.

The present variety of nectarine tree is still further characterized by fruit having discernibly more red blush than the Flamekist. As grown on the aforesaid ranch, the Flamekist bears fruit which—at commercial maturity—averages fifteen to twenty percent red blush at best, and at worst is full yellow, whereas the present variety bears fruit which—at commercial maturity—averages fifty to seventy-five percent red blush at best, and at worst thirty percent red blush. Additionally, the fruit of the present variety has more skin wax in comparison with the Flamekist, and which—together with the enhanced red blush—imparts to the fruit a brighter, glossier overall external finish and appearance.

BRIEF DESCRIPTION OF THE DRAWING

The drawing is an illustration, by photographic reproduction in color, of separate fruit of the present variety; one such fruit being half cut away to expose the flesh, and with the stone remaining in place.

DESCRIPTION OF THE VARIETY

The botanical details of this new and distinct variety of nectarine tree—with color definitions (except those in common color terms) referenced to Maerz and Paul Dictionary of Color (1950 edition)—are as follows:

TREE

Size: Large.
Vigor: Vigorous.
Growth: Upright when young; spreading at maturity.
Production: Productive.
Bearing: Regular bearer.

TRUNK

Size: Medium.
Surface thickness and texture: Medium.
Color
*Older bark.*—Grey-brown (8-E-10).
Lenticels: Numerous.

BRANCHES

Size: Medium.
Surface texture: Medium.
Color
*New wood.*—Green (19-I-6).
*Mature wood.*—Brown (15-E-8).

LEAVES

Size: Medium.
*Average length.*—16.8 cm.
*Average width.*—4.5 cm. (Average measurements from leaves at midpoint of vigorous shoots).
Form: Lanceolate. Tip acute to acuminate. Leaf blade often slightly recurved downward.
Petiole: Medium size.
*Average length.*—12.5 mm.
*Average thickness.*—1.0 mm.
*Color.*—Green (18-I-4).
Stem glands: Medium size. Reniform. Light green (18-H-6) when young. Number range — 3 to 4. Positioned usually on base of leaf margin. Alternate.
Margin: Broadly crenate. Tipped with small brown (16-C-10) gland. Moderately undulated.
Stipules:
*Average number.*—2 at base of petiole.
*Average length.*—11–13 mm. Green (18-J-6), darkening with age. Early deciduous.
Color:
*Top side.*—Dark green (23-L-8).
*Under side.*—Lighter green (21-I-6).

FLOWER BUDS

Size: Medium.
Length: Medium.
Form: Conic.
Pubescence: Moderate.
Hardiness: Hardy for California conditions.

FLOWERS

Date of first bloom: Feb. 26, 1983.
Date of full bloom: Mar. 3, 1983. Medium, as compared with other varieties and very similar to Flamekist.
Size: Large. Diameter range when fully open — 43–44 mm.
Type: Showy.
Color: Light pink (1-D-1).
Bloom: Abundant — 1 to 2 per node.
Pedicel: Short. Length range — 2 to 4 mm. Green (20-J-5), at times tinged with red depending on exposure. Glabrous.
Nectarines: Orange (11-B-10) darkening with age.
Petals:
*Size.*—Large.
*Form.*—Broadly ovate. Cupped.
*Length range.*—17 To 20 mm.
*Width range.*—15 To 17 mm.
*Color.*—Light pink (1-D-1) basally becoming darker pink (1-E-1) with age.
*Margin.*—Wavy.
*Type.*—Showy.
Stamens:
*Length range.*—11 To 14 mm. White, becoming pink (2-B-2) basally at maturity.
*Number range.*—50 To 53.
Anthers:
Medium size.
Medium plump.
Red (2-J-5) dorsally.
Light buff (11-J-4) ventrally.
Abundant yellow (10-J-2) pollen.
Pistil: Average length (fully extended) — 20 mm. Light green-yellow (17-J-2).

FRUIT

Maturity when described:
*Full commercial maturity.*—Sept. 2, 1982.
Date of first picking: Aug. 24, 1982.
Date of last picking: Sept. 3, 1982.
Size: Uniform. Large.
*Average diameter axially.*—69 mm.
*Average transversely in suture plane.*—68 mm.
*Average cheek diameter.*—68 mm.
Form: Nearly round to ovate in lateral aspect — uniform. Globose in axial aspect. Symmetrical to slightly uneven.
Suture: A shallow line extending from base to apex and slightly beyond apex 7 to 15 mm. Slightly deeper and creased along a 10 to 15 mm. area from stem scar to basal shoulder. Slightly deeper along a 20 to 30 mm. area from apex to below apical shoulder. Marked depression beyond pistil point.
Ventral surface:
Rounded. Slightly lipped, usually stronger on one side along entire surface. Lips usually slightly unequal.
Stem cavity: Oval in axial aspect. Medium depth.
*Depth range.*—10 To 15 mm.
*Width range.*—16 To 20 mm.
*Length range.*—22 To 26 mm. Ventral suture deeply although narrowly creased within cavity depression.
Base: Generally rounded. At right angle to fruit axis.
Apex: Rounded.
Tip: Depressed.
Pistil point: Oblique.
Stem: Medium length and medium thickness.
*Length range.*—10 to 15 mm.
*Thickness range.*—3 to 3.5 mm. Yellow (10-J-3)

SKIN

Thickness: Moderately thick.
Texture: Medium.
Tenacity: Tenacious to flesh.
Acidity: low when fully mature.
Tendency to crack: None observed.

Color:

*Ground color.*—Yellow (9-J-2) on unblushed surfaces.

*Blush color.*—Red (2-J-10) to dark red (6-L-2) on thirty to seventy-five percent of the fruit surface. Blush color occurs over some areas as a netted pattern of light and dark coloration rather than as a solid block of color.

Pubescence: Wanting.

Surface: Waxy. Glossy. Bright. Attractive.

Lenticels: Inconspicuous.

FLESH

Color: Yellow (10-J-2) with red flecking.

*Surface of pit cavity.*—Dark red (7-J-5) with some white fibers.

Texture: Firm. Meaty.

Juice: Moderate when fully mature.

Ripens: Evenly.

Fibers: Average number. Fine. Tender.

Flavor: Good. Mild. Slightly acid until fully ripe.

Eating quality: Good.

Aroma: Slight. Pleasant.

STONE

Type: Clingstone. Adheres to flesh over essentially entire surface.

Size: Medium.

*Average length.*—39 mm.

*Average width.*—26 mm.

*Average thickness.*—20 mm.

Form: Roughly obovate in lateral aspect.

Base: Somewhat truncate. Slightly oblique to axis.

Hilum: Medium size. Oval.

Apex: Rounded. Tip sharp, cuspidate.

Sides: Variable, equal to unequal. At times curved either right or left.

Ridges: Numerous over axial shoulder in lateral aspect, usually parallel to apex edge, down to mid-stone. Deep grooves near apex with tops of ridges relatively smooth. Some short and shallow grooves over basal shoulder area converging basally.

Pits: Circular to irregular.

Ventral edge: Wide, with coalesced short wings converging apically. Relatively smooth in outline from apex to base.

Dorsal edge: Moderately full with tight groove extending from base to apex. Apical shoulder moderately eroded. Protrudes, at times strongly, in an area from midway along edge to 10 to 15 mm. back toward apical end.

Color: Dark brown (8-H-8) with some stones slightly tinged with purple.

Tendency to split: None observed.

USE

Fresh market for both local and long distance shipping.

KEEPING QUALITY

Good.

SHIPPING QUALITY

Good.

RESISTANCE TO INSECTS AND DISEASES

No unusual susceptibilities noted.

The nectarine tree and its fruit herein described may vary in slight detail due to climatic and soil conditions under which the variety may be grown; the present description being of the variety as grown in the Central Valley of California.

I claim:

1. A new and distinct variety of nectarine tree, substantially as illustrated and described, particularly characterized, in comparison with the Flamekist, by late-ripening, clingstone fruit which, at commercial maturity, has more red blush and more skin wax, whereby the fruit has a brighter, glossier overall external finish and appearance.

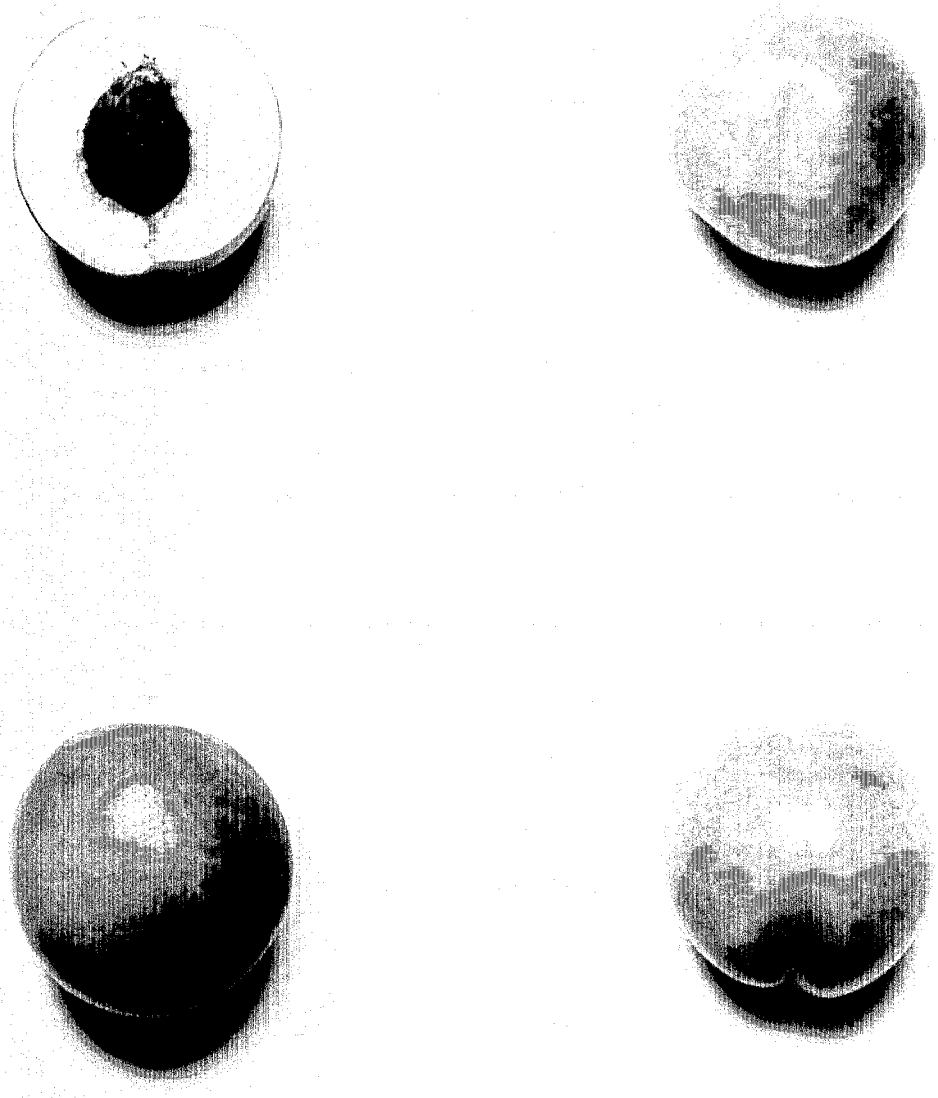

* * * * *